(12) United States Patent
Iwatschenko et al.

(10) Patent No.: US 11,123,513 B2
(45) Date of Patent: Sep. 21, 2021

(54) HUMIDIFIER FOR HUMIDIFYING AN AEROSOL

(71) Applicant: Fraunhofer-Gesellschaft zur Förderung der angewandten Forschung e.V., Munich (DE)

(72) Inventors: Peter Iwatschenko, Eckenthal (DE); Gerhard Pohlmann, Meerbeck (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 700 days.

(21) Appl. No.: 15/123,559

(22) PCT Filed: Mar. 2, 2015

(86) PCT No.: PCT/EP2015/054240
§ 371 (c)(1),
(2) Date: Sep. 2, 2016

(87) PCT Pub. No.: WO2015/132172
PCT Pub. Date: Sep. 11, 2015

(65) Prior Publication Data
US 2017/0072161 A1 Mar. 16, 2017

(30) Foreign Application Priority Data
Mar. 5, 2014 (EP) .................................... 14157788

(51) Int. Cl.
*B05B 1/06* (2006.01)
*B05B 1/24* (2006.01)
(Continued)

(52) U.S. Cl.
CPC ...... *A61M 16/142* (2014.02); *A61M 16/0808* (2013.01); *A61M 16/109* (2014.02);
(Continued)

(58) Field of Classification Search
CPC ............ A61M 11/005; A61M 16/0808; A61M 16/0883; A61M 16/105; A61M 16/109;
(Continued)

(56) References Cited

U.S. PATENT DOCUMENTS 3,871,373 A * 3/1975 Jackson ................ A61M 15/08
128/203.27
4,318,398 A * 3/1982 Oetjen .............. A61M 16/1045
128/201.13
(Continued)

FOREIGN PATENT DOCUMENTS

EP 0397446 11/1990
EP 0764172 3/1997
(Continued)

OTHER PUBLICATIONS

International Search Report and Written Opinion, dated Apr. 10, 2015, International Patent Application No. PCT/EP2015/054240 (17 pages).
(Continued)

*Primary Examiner* — Justine R Yu
*Assistant Examiner* — Matthew D Ziegler
(74) *Attorney, Agent, or Firm* — Hamre, Schumann, Mueller & Larson, P.C.

(57) ABSTRACT

The invention relates to a humidifier configured to humidify an aerosol, the humidifier comprising a first water compartment (100) containing water used to humidify the aerosol; a second water compartment (300) containing water used to humidify the aerosol; an intermediate chamber (200) located between the first and the second water compartment (100, 300), the intermediate chamber (200) comprising an aerosol inlet (210) and an aerosol outlet (220) and providing first boundary surfaces of a passageway (230) through which the aerosol to be humidified passes; a first layer (10) permeable
(Continued)

to water vapour and impermeable to liquid water, which is located between the first water compartment (100) and the intermediate chamber (200), wherein a section of the first layer provides a second boundary surface of the passageway; a second layer (20) permeable to water vapour and impermeable to liquid water, which is located between the second water compartment (300) and the intermediate chamber (200), wherein a section of the second layer provides a third boundary surface of the passageway (230) opposed to the second boundary surface.

18 Claims, 6 Drawing Sheets

(51) Int. Cl.
| | | |
|---|---|---|
| B05B 12/10 | (2006.01) | |
| A61M 16/14 | (2006.01) | |
| A61M 16/08 | (2006.01) | |
| A61M 16/16 | (2006.01) | |
| A61M 16/10 | (2006.01) | |
| A61M 11/00 | (2006.01) | |

(52) U.S. Cl.
CPC .......... *A61M 16/16* (2013.01); *A61M 16/162* (2013.01); *B05B 1/06* (2013.01); *B05B 1/24* (2013.01); *A61M 11/005* (2013.01); *A61M 16/0883* (2014.02); *A61M 16/105* (2013.01); *A61M 2202/0488* (2013.01); *A61M 2202/064* (2013.01); *A61M 2205/126* (2013.01); *A61M 2205/127* (2013.01); *A61M 2205/128* (2013.01); *A61M 2205/3368* (2013.01); *A61M 2205/366* (2013.01); *A61M 2205/3653* (2013.01); *A61M 2205/7536* (2013.01); *A61M 2206/11* (2013.01); *B05B 12/10* (2013.01)

(58) Field of Classification Search
CPC .. A61M 16/142; A61M 16/16; A61M 16/162; A61M 2202/0488; A61M 2202/064; A61M 2205/126; A61M 2205/127; A61M 2205/3653; A61M 2205/3368; A61M 2205/366; A61M 2205/7536; A61M 2206/11; A61M 16/14; A61M 16/147; B05B 12/10; B05B 1/06; B05B 1/24
USPC ............ 128/203.12, 203.16, 203.17, 204.14, 128/204.17
See application file for complete search history.

(56) References Cited

U.S. PATENT DOCUMENTS

| | | | | |
|---|---|---|---|---|
| 4,829,997 A * | 5/1989 | Douwens | .......... | A61M 16/1075 128/201.13 |
| 4,910,384 A | 3/1990 | Silver | | |
| 4,943,704 A * | 7/1990 | Rabenau | ............... | A61M 16/16 261/104 |
| 5,062,145 A * | 10/1991 | Zwaan | .................. | A61M 16/16 392/396 |
| 6,135,432 A * | 10/2000 | Hebblewhite | ............. | F24F 6/02 261/119.1 |
| 6,201,223 B1 * | 3/2001 | Nitta | ................. | A61M 16/1075 219/544 |
| 7,708,013 B2 * | 5/2010 | Niland | .................. | B01F 5/0476 128/201.13 |
| 7,753,991 B2 * | 7/2010 | Kertzman | ......... | A61M 16/1045 128/203.22 |
| 8,418,690 B2 * | 4/2013 | Power | ............... | A61M 16/0672 128/203.15 |
| 8,550,075 B2 * | 10/2013 | Virr | ..................... | A61M 16/202 128/203.27 |
| 8,910,627 B2 * | 12/2014 | Iwatschenko | .......... | A61M 11/02 128/203.12 |
| 10,213,573 B2 * | 2/2019 | Smith | .................... | A61M 16/14 |
| 2004/0254524 A1 | 12/2004 | Spearman et al. | | |
| 2006/0021615 A1 | 2/2006 | Kertzman | | |
| 2007/0267010 A1 * | 11/2007 | Fink | ..................... | A61M 11/005 128/200.23 |
| 2008/0021377 A1 * | 1/2008 | Kienman | ............ | A61M 1/1696 604/29 |
| 2011/0120468 A1 | 5/2011 | Doyle | | |
| 2011/0285038 A1 * | 11/2011 | Lin | ..................... | A61M 1/1698 261/101 |
| 2012/0090606 A1 * | 4/2012 | Iwatschenko | .......... | A61M 11/02 128/203.15 |
| 2012/0247464 A1 * | 10/2012 | Poole | ................ | A61M 15/0028 128/203.15 |

FOREIGN PATENT DOCUMENTS

| | | |
|---|---|---|
| EP | 0877602 | 11/1998 |
| JP | H03-01880 | 1/1991 |
| JP | 08-178376 | 7/1996 |
| JP | 10-015070 | 1/1998 |
| JP | 2001-340460 | 12/2001 |
| JP | 2012-503518 | 2/2012 |
| JP | 2013-540704 | 11/2013 |
| RU | 93027705 | 11/1995 |
| WO | 92/06703 | 4/1992 |
| WO | 2006/108558 A1 | 10/2006 |
| WO | 2010/035251 | 4/2010 |
| WO | 2010/122103 | 10/2010 |
| WO | 2012/025496 | 3/2012 |
| WO | 2013/132056 | 9/2013 |

OTHER PUBLICATIONS

Japanese Office Action, issued in the corresponding Japanese patent application No. 2016-555498, dated Nov. 20, 2018, 10 pages.

* cited by examiner

HUMIDIFIER FOR HUMIDIFYING AN AEROSOL

TECHNICAL FIELD

The present invention relates to a humidifier configured to humidify an aerosol.

BACKGROUND

In devices for aerosolization of aerosolizable dry material, the aerosolizable material, e.g. a powdered pharmaceutical substance, is acted upon with a compressed gas or carrier gas in a specially provided chamber and, by entraining of the particles into a gas stream, is converted within this chamber to a state which is referred to as aerosol. The particles of the dry material are present across the entire volume of the compressed gas, preferably in a uniform and finely dispersed form.

In a pharmaceutical context, such devices are used for inhalative administration of pharmaceutical preparations to both patients which are breathing normally and to mechanically ventilated patients and patients under ventilatory support alike. In the first case, typical examples for such devices are handheld dry powder inhalers (DPIs) and metered dose inhalers (MDIs). In case of patients under mechanical ventilation or ventilatory support, the inhaler per se must be integrated into, or be attached to, the ventilatory circuit which comprises the ventilator, the tubings from the ventilator to the patient interface and back, and the patient interface which usually is a suitable mouthpiece, a breathing mask, a nasal canula or a tracheal canula.

As the name already suggests, pharmaceutical preparations in form of an inhalable dry powder can be administered by dry powder inhalers (DPIs). A limitation of these devices is the quantity of a pharmaceutical preparation which is to be administered. DPIs as known today are typically capable of aerosolizing amounts of dry powder in the milligram range. While this is sufficient for many medications, there are pharmaceutical preparations which require the administration of significantly larger amounts. One example are lung surfactant preparations, which usually need to be administered in amounts of up to several grams. Using conventional dry powder inhalation devices, administration to a patient of one gram or more of a pharmaceutical preparation would require unacceptably long inhalation times. In order to solve this problem, the dry powder aerosolization apparatus described in WO 2006/108558 was devised which allows the aerosolization of several grams of powdered substance in the course of a couple of minutes. Thus this device is a good choice when large amounts, several hundred milligrams or more, of a pharmaceutical preparation are to be administered as an aerosol. A further issue of devices known to the art which provide an aerosol is the reproducibility and the dose of the amount of aerosolized material delivered to the patient. This is particularly the case when during storage or even during use of the device the particles of the aerosolizable material agglomerate to large particles with a different aerodynamic behavior. Particles having a larger than optimal aerodynamic diameter (which is approx. 1-5 µm) will have a much smaller chance to reach the target, e.g. the lung alveoles, since they tend to be deposited in the upper airways or throat or even somewhere in the inhaling apparatus already. Given that such unwanted deposition is almost impossible to quantify during treatment of a patient, too high a degree of unwanted deposition renders it impossible to determine the exact dose of the substance to be administered which reached the target organ.

In vertebrates, the inner lung surfaces involved in gas exchange are covered by a thin film of a substance mixture called "pulmonary surfactant" or "lung surfactant". The most important components of lung surfactant are phospholipids and the so-called surfactant proteins, SP-A, SP-B, SP-C and SP-D. Lung surfactant has surface active properties and reduces surface tension in the alveoli and small airways to such an extent that collapse of the alveoli during exhalation is avoided. The surface tension is regulated dynamically so that the collapse of the alveoli and small airways in favor of the greater ones, which is to be expected according to Laplace's law, is prevented by appropriate adaptation of the surface tension. On the other hand, reduction of surface tension in the alveolar region increases pulmonary compliance, meaning that it facilitates the expansion of the lung upon breathing. The presence of lung surfactant results in a well-balanced and physiologically stable structure of the lung and is vital for the normal function of this organ. While at the time of birth the lungs of mammals contain a sufficient amount of endogenous lung surfactant in order to ensure unrestrained functionality of the lungs from the first breath on, the lungs of prematurely born babies (born below 32 weeks of gestation and especially born below 29 weeks of gestation) are not or not sufficiently capable of producing lung surfactant. This leads to a life-threatening deficiency of oxygen uptake (Infant Respiratory Distress Syndrome, IRDS). IRDS is the main cause of death in prematurely born babies.

Lung surfactant preparations useful to treat Respiratory Distress Syndrome (RDS) such as IRDS can be obtained from the lungs of animals or can be manufactured using the individual components as starting material. For example, WO 92/06703 describes the production of synthetic lung surfactant preparations by evaporating chloroform from a solution comprising phospholipids (such as dipalmitoyl-phosphatidylcholine (DPPC) and dioleylphosphatidyl-ethanolamine (DOPE)) and cholesterol using a rotary evaporator to obtain a thin film which is resuspended in a buffer, if desired together with suitable proteins. EP 0 877 602 discloses the preparation of a synthetic lung surfactant by spray drying a solution of DPPC, palmitoyloleoylphosphatidylglycerol (POPG), palmitic acid, calcium chloride and surfactant protein SP-C.

It was found that inhalation of an aerosol formed by aerosolization of dry powder lung surfactant preparations in dry air tends to lead to formation of unwanted depositions, once the aerosol comes into contact with the moist surface of the tissue lining the airways. Such deposits formed in the airways may reach a size that threatens to clog the bronchi, the trachea, or other parts of the airways, thus posing a serious suffocation risk to the patient. Once such deposition has begun, a rapid build-up of a formed clog is observed.

WO 2012/025496 describes a system in which particles are provided in an aerosolized form which, before inhalation by the patient but after aerosolization, are subjected to a humidification step. It surprisingly turned out that upon inhalation of an aerosol containing particles with sufficient water on their surface forms much less aggregates than an aerosol of essential dry particles. However, WO 2012/025496 is silent regarding the structural details of humidifiers specially adapted to the process of generating such humidified particles, and, in particular, regarding useful geometries of such humidifiers.

SUMMARY

Accordingly, a need exists to provide a humidifier which is able to effectively humidify an aerosol. As used herein, "aerosol" usually will mean essentially dry particles suspended in a gas phase, for example particles of a pharmaceutical preparation such as, e.g., lung surfactant, suspended in air. However, as will be seen by the person skilled in the art, aerosol particles don't necessarily need to be solid, but could be liquid as well. In such case the aerosol would comprise droplets of a solution, a suspension or a melt suspended in a gas phase.

The need mentioned above is met by the features of the independent claim. Further embodiments are described in the dependent claims.

According to a first aspect, a humidifier configured to humidify an aerosol is provided, the humidifier comprising a first water compartment containing water used to humidify the aerosol and a second water compartment containing water used to humidify the aerosol. An intermediate chamber (or "middle chamber") is located between the first and the second water compartments and comprises an aerosol inlet and an aerosol outlet, the intermediate chamber furthermore providing first boundary surfaces of a passageway through which the aerosol to be humidified passes. The humidifier furthermore contains a first layer permeable to water vapour and impermeable to liquid water (a "semipermeable" layer) which is located between the first water compartment and the intermediate chamber. A section of this first layer provides a second boundary surface (in form of a semipermeable wall) of the passageway. The humidifier contains a second layer permeable to water vapour and impermeable to liquid water which is located between the second water compartment and the intermediate chamber. A section of the second layer provides a third boundary surface (in form of a semipermeable wall) of the passageway opposed to the second boundary surface.

This humidifier with the two water compartments and the two layers provides an effective device to humidify the aerosol. Water vapour can pass from the water compartment through the corresponding layer into the intermediate chamber where the aerosol is humidified. Furthermore, by controlling the temperature and thus the vapour pressure in the first water compartment and the second water compartment, the aerosol to be humidified can be heated on its passage through the intermediate chamber. Through the fact that the first layer and the second layer build a part of the passageway, a large surface is provided where the water vapour and the aerosol come into contact with each other. Furthermore, with the water compartments on opposed side surfaces (in form of semipermeable walls) of the intermediate chamber a homogeneous humidification of the aerosol is obtained, thus minimizing particle losses.

The intermediate chamber may have a substantially cylindrical shape and the aerosol outlet can be located on a lateral surface of the intermediate chamber. This means that the aerosol does not pass through the intermediate chamber in an axial direction of the cylindrically shaped intermediate chamber, but the aerosol inlet and outlet are provided on a lateral surface and not on an axial end surface of the humidifier. Furthermore the aerosol inlet and aerosol outlet are located substantially at the same height on the lateral surface in the axial direction. The passageway delimited by the first boundary surfaces, the second boundary surface and the third boundary surface can be located in the intermediate chamber in such a way that the aerosol passing through the passageway is mainly flowing perpendicular to an axial direction defined by the substantially cylindrical shape of the intermediate chamber.

The second boundary surface and the third boundary surface, through which the aerosol to be humidified is humidified by the water vapour passing through the corresponding semipermeable wall of the boundary surface are located parallel to each other on opposite sides of the passageway. As will be explained below, this geometrical arrangement helps to avoid deposition of particles of the aerosol in the passageway. When water vapor enters the passageway through the semipermeable wall, a momentum is transferred onto the particles contained in the passageway in the direction in which the water vapor is travelling through the semipermeable wall. Thus, if only a single boundary surface through which water vapor enters the passageway was provided, particles of the aerosol would be deposited on the opposite side surface opposite to the wall through which the water vapor enters the passageway. In the present case however, such deposition of particles on the opposite wall is avoided since water vapor enters the passageway from opposite sides with the result that the effective momentum transfer is zero. The water vapor entering the passageway from the first water compartment and from the second water compartment have an opposite momentum so that the effective momentum applied to the aerosol in the passageway is zero. As a consequence, a deposition of particles in the passageway can be effectively avoided or reduced.

Preferably, the aerosol inlet, the passageway, and the aerosol outlet are arranged in such a way that the aerosol exiting the aerosol outlet has a flow direction which is opposite to the flow direction of the aerosol entering the aerosol inlet. In other words, this means that the aerosol inlet and the aerosol outlet are provided on the same half of the lateral surface. Preferably, the chamber is arranged in such a way that the axis of the cylindrically shaped chamber extends in the horizontal direction. This results in an upper lateral surface and a lower lateral surface. Preferably, the aerosol inlet and the aerosol outlet are provided on the upper lateral surface. It is especially beneficial to provide the aerosol outlet on the upper lateral surface in order to prevent any condensed liquid which may be generated in the intermediate chamber from being transported together with the aerosol to the inhaling patient, as the liquid will be naturally collected in a lower part of the lateral surface of the intermediate chamber. For the removal of this condensed liquid the passageway may furthermore contain an opening which is also located in the lateral surface of the intermediate chamber. Preferably, the opening is provided on part of the lateral surface which is opposite to the part of the lateral surface where the aerosol inlet and aerosol outlet are provided. With a horizontal orientation of the axis of the intermediate chamber the opening may be provided at a lower part of the lateral surface whereas the inlet and the outlet are provided on an upper part of the lateral surface.

The intermediate chamber may furthermore comprise at least one protrusion protruding from the lateral surface of the intermediate chamber to its inside. This at least one protrusion can be part of the first boundary surfaces and provides a support surface for each of the first layer and second layer. Furthermore, at least two protrusions may be provided instead of one protrusion which each protrude from the lateral surface of the intermediate chamber to its inside. The at least two protrusions build further surfaces (or walls) of part of the passageway and are part of the first boundary surfaces and protrude to the inside of the intermediate chamber in such a way that the passageway follows a meandering pattern inside the intermediate chamber between the at least two protrusions. This means that the two protrusions may protrude from opposite parts of the inner lateral surface to the inside.

The first layer which rests on a first support surface of the provided protrusions and the second layer resting on a second support surface of the protrusions seal neighbouring sections of the passageway from each other in an axial direction of the intermediate chamber. This means that the aerosol flowing through the passageway has to flow around the different protrusions so that a defined flow path inside the intermediate chamber is provided.

The humidifier may be used in connection with an aerosolization device and the humidified aerosol is provided to a patient who is either a mechanically ventilated patient or who is an actively breathing patient. When the humidifier is used in connection with an actively breathing patient, the intermediate chamber may furthermore have a second inlet in the passageway configured for the inlet of additional breathing air into the passageway. The breathing gas within the passageway can then be humidified and heated if necessary together with the aerosol. Seen in a direction of the flow of the aerosol in the passageway, this second inlet may be located after the aerosol inlet. Furthermore, the second inlet may be arranged angled relative to the first inlet so that the aerosol and the breathing air do not enter the intermediate chamber in two parallel flows. This angle of the second inlet relative to the first inlet assures that the breathing air can mix with the aerosol.

In one embodiment, each of the first and second water compartments may contain a heating unit which is used to heat the water in the corresponding compartment. In another embodiment, a water circuit may be provided which circulates hot water through the first and the second water compartments. The water circuit can have a pump for pumping the water through the water circuit and a heat exchanger which can be used to heat the water.

The water in each water compartment should preferably have a substantially constant temperature inside the water compartment. Each water compartment may comprise projections which guide the water circulating in the corresponding water compartment and which help to circulate the water inside the compartment in such a way that a substantially uniform temperature is obtained inside the water compartment. The projections provided in each of the water compartments each build a further support surface for the first or for the second layer. The first layer is furthermore preferably arranged substantially parallel to the second layer. With such an arrangement, a mirror symmetric arrangement of the humidifier may be obtained.

It is furthermore possible that a nozzle is provided at the aerosol inlet through which the aerosol to be humidified enters the passageway. Such nozzle then has a cross-section which increases in the flow direction of the aerosol and the nozzle comprises as inner walls at least one excitable membrane which is configured to be excited by pressure pulses. In a preferred setup the aerosol to be humidified by a humidifier according to the present invention is generated by a device as disclosed in WO 2006/108558 or in WO 2010/122103. In such devices, pulses of pressurized air are used to suck aerosolizable material out of a reservoir and to entrain the material in an air flow, such that an aerosol is formed. These pressure pulses introduced in the aerosol's flow path then can be also used to excite the excitable membrane forming the inner walls of the nozzle, very much like they are used in a device according to WO 2010/122103 to excite the inner walls of the reservoir used for storing the aerosolizable material, the inner walls of the aerosolization channel and/or the inner walls of a hollow spacer. The excitable membrane in the nozzle helps to prevent particles in the aerosol from adhering to the aerosol inlet and so helps to prevent agglomeration of particles at the aerosol inlet. Preferably, the nozzle has a conical shape and the opening angle of the nozzle may be between 5° and 50°, preferably between 7° and 11°, more preferably between 8° and 10°, and even more preferably 9°. The pressure pulses may be the pressure pulses that are used to generate the aerosol from the aerosolizable material.

The invention will be described in further detail with reference to the accompanying drawings.

DETAILED DESCRIPTION

Figure 1:
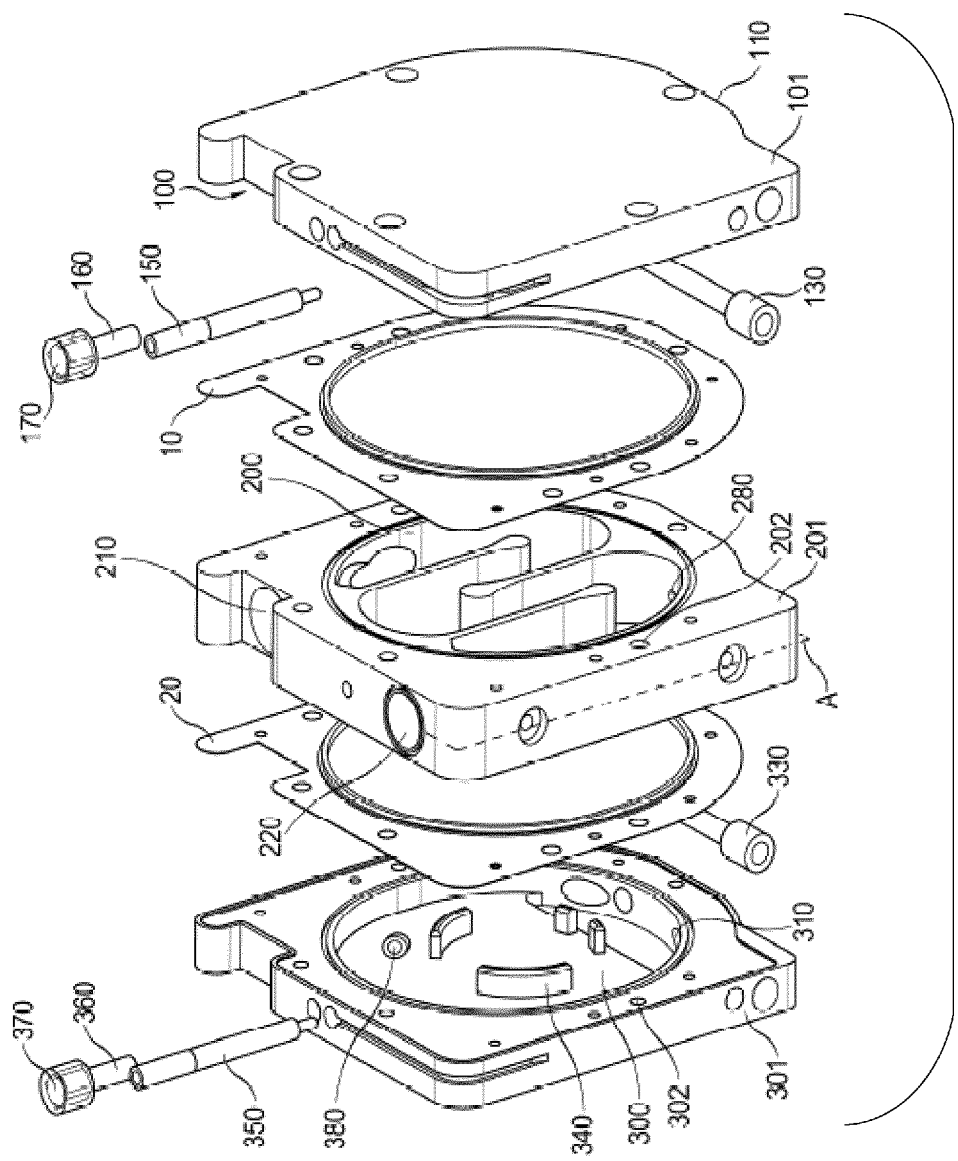
FIG. 1 shows an exploded view of a humidifier configured to humidify an aerosol.

Referring to the drawings, a humidifier that can be used to humidify an aerosol will be explained in more detail.

The humidifier comprises a first water compartment 100 containing water used to humidify an aerosol flowing through an intermediate chamber 200. The humidifier furthermore contains a second water compartment 300, the second water compartment also containing water used to humidify the aerosol. The intermediate chamber is sandwiched between the first water compartment 100 and the second water compartment 300. Between the first water compartment 100 and the intermediate chamber 200 a first layer 10 is provided which is permeable to water vapour but impermeable to liquid water. A second layer 20 permeable to water vapour but impermeable to liquid water is provided between chamber 200 and the second water compartment 300.

An aerosol to be humidified enters the intermediate chamber via an aerosol inlet 210. A passageway 230 is built in the intermediate chamber as shown inter alia in FIG. 3. The aerosol is humidified on its passage through the passageway from the aerosol inlet 210 to an aerosol outlet 220. When the aerosol enters the aerosol inlet 210, the aerosol is essentially dry (provided the aerosol has been generated by aerosolization of an essentially dry powder). In the present context, "essentially dry" refers to a water content of the particles contained in the aerosol in their typical storage form of dry powders to be aerosolized in commercially available aerosolizers. Typically the water content of such a dry powder is no more than 5% w/w, no more than about 3% w/w, no more than about 2% w/w or even no more than about 1% w/w. Essentially dry particles are particles which are readily aerosolizable, in particular using an aerosolization device as described inter alia in WO 2006/108558 or WO 2010/122103 A1. Prior to being suspended in a carrier gas in the aerosolization device, the essentially dry inhalable particles form a powder. In the aerosolization device known from the art, this dry powder is turned into an aerosol by suspending the dry particles in a carrier gas. This essentially dry aerosol enters the humidifier through the aerosol inlet 210 where water vapour is added to the aerosol to obtain a humidified aerosol having a higher water content at the aerosol outlet 220 than at the aerosol inlet 210.

The particles can be an essentially dry powder as mentioned above. In order to maximize the inhalable fraction of particles (i.e., the fraction of the particles which, upon inhalation, are transported to and deposited in the deep lung), the particle's mass median aerodynamic diameter (MMAD) in the aerosol may be between 0,1 and 10 μm, preferably between 1 and 5 μm or approximately 3 μm. The particles contain a therapeutically active substance which can be any substance having a desired therapeutic effect upon inhalation including lipids such as phospholipids, small molecule drugs, peptides, proteins such as surfactant proteins or synthetic analogs thereof, enzymes or antibodies, nucleic acids such as siRNA, and so forth. The therapeutically active substance can also be any mixture of substances which has a desired therapeutic effect upon inhalation, such as natural or artificial lung surfactant. For example, the therapeutic effect of the therapeutically active substance may be exerted by physical interaction with the lung tissue (as is the case with lung surfactant), by the binding of a molecule to a receptor, by inhibition or activation of an enzyme, by enzymatic action per se, by the binding of an antibody to a specific epitope, by RNA interference, by interacting with a pathogen present in the airways (including interaction with the pathogen's replication, toxin production and/or toxin secretion) and so forth, regardless of whether the desired therapeutic effect takes place in the lung (or other parts of the airways) already or at other locations of the body which, subsequent to inhalation and uptake, are reached by the therapeutically active substance via the vascular system. Non-limiting examples for therapeutically active substances that can advantageously be used according to the invention are both short and long acting beta-adrenoceptor agonists, glucocorticoids and other steroids (e.g., Ciclesonide), phosphodiesterase inhibitors such as, e.g., PDE4 inhibitors (in particular Roflumilast) or PDE5 inhibitors (e.g., Sildenafil), anticholinergics, natural or artificial lung surfactant, DNAse (e.g., Pulmozyme), insulin, antibiotics, cytostatic compounds, anti-inflammatory compounds, mucolytic compounds, and any other therapeutically active substance that can advantageously be administered to the lungs of a patient. In a preferred embodiment the therapeutically active substance is lung surfactant which exerts its therapeutic effect at least in part by physical interaction with the lung tissue, namely by a reduction of the surface tension in the alveoli. In another preferred embodiment, the particle according to the invention comprises more than one therapeutically active substance. In a particularly preferred embodiment, the particle according to the invention comprises more than one therapeutically active substance, one of them being lung surfactant.

"Lung surfactant" (or "pulmonary surfactant") means any pharmaceutically acceptable substance or composition which is capable of fulfilling at least part of the normal functions of natural mammalian (in particular human) lung surfactant. Lung surfactant preparations may be obtained by extraction from natural tissues (e.g., bovine, ovine or porcine lung) or can be manufactured from individual ingredients such as phospholipids, lung surfactant proteins or derivatives thereof (including artificial lung surfactant proteins such as the KL4 polypeptide), fatty acids, salts and other components. Commercially available lung surfactants comprise Alveofact, Curosurf, Exosurf, Infasurf, Pumactant (ALEC), Surfaxin, and Survanta. At least one further lung surfactant, Venticute, has been under clinical investigation. Certain artificial lung surfactant compositions mimic natural lung surfactant by containing phospholipids and at least one recombinant derivative of surfactant protein SP-C such as the FF/I mutant called "rSP-C" (INN Lusupultide, known from EP 0 764 172), which is a truncation derivative of human SP-C which carries three point mutations. In a particularly preferred application of the present invention the therapeutically active substance (or one of the therapeutically active substances, if the particles comprise more than one therapeutically active substance) is lung surfactant which has been manufactured by spray drying and comprises DPPC, POPG, rSP-C, palmitic acid, and calcium chloride. In a further particularly preferred application the therapeutically active substance is lung surfactant which has been manufactured according to the teaching of EP 0 877 602.

An important use of lung surfactant aims at performing at least parts of the role of natural, endogenous lung surfactant. This can be particularly important when a patient suffers from a deficiency of endogenous lung surfactant. Lung surfactant can then be administered to the patient's lungs in order to replace the missing or damaged (e.g., in case of aspiration of gastric contents, by proteolytic activity) endogenous surfactant ("surfactant replacement therapy"). Examples where the function of endogenous lung surfactant is impaired are acquired respiratory distress syndrome (ARDS), IRDS, idiopathic pulmonary fibrosis, cystic fibrosis, chronic obstructive pulmonary disease (COPD) (in particular COPD exacerbations), and chronic bronchitis. A further example is lung surfactant deficiency of preterm neonates (in particular of neonates born below 32 or even below 29 weeks of gestation).

Returning to FIGS. 1, 2, and 3, the aerosol containing the active substance entering the chamber 200 is brought into contact with water vapour provided by the two opposite water compartments 100 and 300.

The carrier gas in which the therapeutically active substance is provided (and which together with the therapeutically active substance provides the aerosol) may be air, for example medicinal air, and may be standardized air available in any hospital. In order to avoid adherence of the particles to be aerosolized during the aerosolization process, the relative humidity of the carrier gas used to generate the aerosol is preferably 20% or lower. Even more preferably, the relative humidity of the carrier gas is less than 10%. As a consequence, the aerosol entering the aerosol inlet 210 will be rather dry. The relative humidity of the aerosol (or more precisely: of the aerosol's carrier gas) passing through the chamber 200 will be increased from less than 10% or 20% to just below 100% or more, generally speaking to a value which is close to the dew point, by bringing the aerosol into contact with water vapour. As will be described in further detail below, the water vapour is generated by the first water compartment 100 and the second water compartment 300 through which heated water passes.

The two water compartments 100, 300 contain water that usually has been heated to an elevated temperature, e.g. 50-60° C., to increase the water's vapour pressure. The liquid water contained in the first water compartment 100 and the second water compartment 300 is separated from the intermediate chamber by the first layer 10 and the second layer 20 respectively. Both layers provide a semi-permeable barrier which is permeable to water vapour but essentially impermeable to liquid water. By way of example, the semi-permeable barrier is a membrane which is usually made from a synthetic material such as, e.g. Nafion, Goretex or Sympatex. The first layer 10 and the second layer 20 can be made from any material which has the desired properties in order to allow water vapour to enter the aerosol passage while retaining liquid water, and preferably are made of a finely perforated material.

In the embodiment of FIG. 1 the humidifier is shown in an orientation as it may be installed during use. The intermediate chamber has a substantially cylindrical shape with the axis of the cylinder having a horizontal orientation. The aerosol inlet 210 and the aerosol outlet 220 are provided on a lateral surface of the cylindrically shaped chamber 200. In the embodiment shown, the aerosol inlet 210 and the aerosol outlet 220 are provided such that the aerosol on entering the aerosol inlet has a flow direction which is opposite to the flow direction of the aerosol exiting the aerosol outlet. When the cylindrically shaped intermediate chamber 200 is located as shown in FIG. 1 with the axis of the cylinder extending in the horizontal direction, it is assured that the aerosol outlet is located on an upper lateral surface of the intermediate chamber. Outside the intermediate chamber 200 a housing 201 is provided, the housing 201 being designed in such a way that the humidifier can be placed on a horizontal surface or is somehow brought into a stable position. The housing 201 furthermore contains openings, via which the housing 201 of the intermediate chamber can be fixedly connected to the first layer 10, the second layer 20, to a housing 101 of the first water compartment and a housing 301 of the second water compartment using e.g. fixing elements. In the embodiment shown, the housings 301, 201, and 101 are substantially square-shaped. However, it should be understood that any shape may be used. The openings may be holes configured to receive fixing elements such as screws.

As can be seen from FIG. 1, the whole humidifier is designed in such a way that it is mirror symmetric to a plane A which is shown in FIG. 1 and which passes through the intermediate chamber. Plane A has a surface normal parallel to the axial direction of the intermediate chamber and is located at half of the width of the chamber when viewed in the axial direction.

As will be easily understood by a person skilled in the art, throughout the humidifier according to the present invention the passageway will be shaped in a way to reduce or even prevent the occurrence of turbulent flow. Doing so will help to reduce the deposition of aerosolized particles to a minimum. One of the measures to be taken in order to reduce or prevent turbulent flow is to avoid any sharp angles and edges along the aerosol's flow path. This can be seen, for example, at the tips of protrusions 240, 250 and 260, which are made round to accommodate a smooth, laminar flow of aerosol around them.

Figure 2:
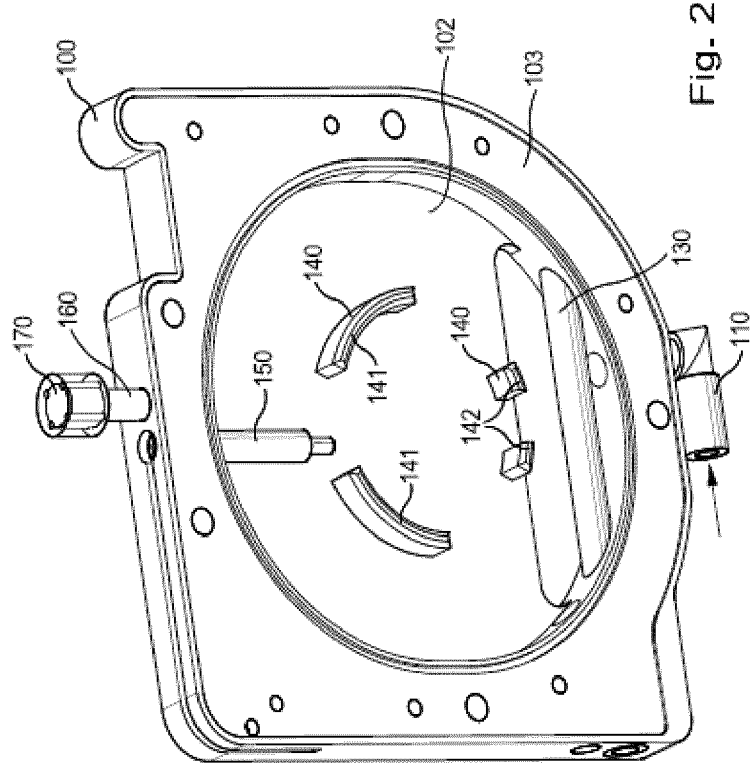
FIG. 2 is a perspective view for a water compartment containing water used to humidify the aerosol.

In connection with FIG. 2, a water compartment containing the water used to humidify the aerosol is explained in more detail. In connection with FIG. 2 the first water compartment 100 is disclosed in more detail. However, as the system is preferred to be mirror symmetric, the explanation given below is also applicable to the second water compartment 300.

The first water compartment 100 is located in a housing 101 and the water compartment is also cylindrically shaped with a water inlet 110 to fill the water compartment with water. In the embodiment shown a heating unit 130 is provided in the water compartment. This heating unit 130 can be a cylindrically shaped body, e.g. made of metal, and may include an electrical heating element to heat the water inside the water compartment. For controlling the temperature of the water inside the water compartment, a temperature sensor 150 may be provided. When the water compartment is filled with water for the first time, the air provided in the water compartment may leave the water compartment through ventilation 160. To avoid the contamination of the water inside the water compartment, a filter 170 may be provided on the ventilation 160. The water compartment 100 furthermore comprises projections 140 which are arranged inside the water compartment in such a way that guidance is provided to the water circulating in the water compartment. The projections help to obtain a homogenous temperature distribution inside the water compartment. The projections 140 furthermore have a second function. The water compartment is closed at one end of the water compartment by an axial end surface 102. The projections 140 extend from this axial end surface 102 in the axial direction of the water compartment in such a way that the end surfaces 101 and 102 are located at the same axial height as the surface 103 of the housing 101 on which the first layer is provided. The surfaces 141 and 142 provide a support for the layer 10 which is an elastic membrane. The projections with support surfaces 141 and 142 help to avoid or to reduce deformation of the membrane.

In the embodiment shown, the water inside the water compartment is heated using heating unit 130. In another embodiment a water circuit may be provided in which water is heated outside the water compartment and passed through the water compartment. Such an embodiment will be described later in further detail in connection with FIG. 6. In such an embodiment, the heating unit 130 need not necessarily be provided as the water in the water compartment can be heated outside the water compartment.

The water in the water compartment can be heated to a temperature which usually is between 37° C. and 100° C., preferably heated to a temperature between 45° C. and 75° C. or a temperature between 50° C. and 60° C. The amount of water vapour passing the phase boundary and entering the intermediate chamber 200 depends on the semi-permeable barrier's permeability of layers 10 and 20, on the liquid water's vapour pressure which depends on temperature and increases with temperature, on the partial pressure of water vapour already present in the gas phase and on the temperature of the gas phase. As the water vapour will have the same temperature as the heated water, the water vapour entering the intermediate chamber 200 will also help heating the aerosol flowing in the intermediate chamber 200. The heating of the aerosol increases the aerosol's capacity for water vapour so that a considerable amount of water vapour can be added to the aerosol. When the desired amount of water vapour has been taken up, the gas phase's water content usually is close to saturation. In practice, heating the aerosol on its passage through the intermediate chamber to a temperature in the range of 50° C.-60° C. turned out to be very advantageous regarding the amount of water available for condensation on the particles before administration to the patient. It should be understood that, before the humidified aerosol is fed to the patient, usually a cooling step will be applied in which the humidified aerosol is again cooled to a second temperature in the range of 15° C.-45° C., preferably to a second temperature above 20° C. and most preferably to a temperature of about 37° C. In this context, reference to WO 2012/025496 is made, which describes the process of preparing humidified aerosols of therapeutically substances in detail.

In connection with FIG. 3, the intermediate chamber through which the aerosol is guided will be explained in more detail. The aerosol, as explained above, will be heated when passing through the intermediate chamber and will be humidified during this passage. A housing 201 is provided which, on the lateral surface, encloses the intermediate chamber 200. The intermediate chamber is also cylindrically shaped with the aerosol inlet 210 provided on the lateral surface of the chamber and the aerosol outlet 220 being provided on the lateral surface of the intermediate chamber. Inside the chamber 200 the aerosol flows along a passageway 230 before it leaves the intermediate chamber. The length of the passageway may be between 10 and 30 cm. However, other lengths are conceivable as well and the lengths depend on the amount of water vapour to be added to the aerosol in the chamber, on the flow velocity of the aerosol and on the aerosol's desired temperature increase. As may be seen in FIG. 1, the passageway is, on the opposed end surfaces of the chamber, closed in the axial direction by the first layer 10 and the second layer 20 respectively. The intermediate chamber comprises several protrusions 240, 250, and 260 which protrude from the lateral surface of the chamber to the inside of the chamber, thus building first boundary surfaces of the passageway. In the embodiment shown, the first section of the passageway is formed after the air inlet in a radial direction of the chamber by the outer surface of the chamber and by a first surface 241 of protrusion 240. The protrusions extend in the axial direction of the chamber over the entire axial extension of the chamber. The protrusions furthermore contain in the axial direction end surfaces 243. These end surfaces provide support surfaces for the first and second layer 10, 20. One of the axial end surfaces 243 provides a support surface for one of the two layers 10 or 20, whereas the other (opposite) support surface 243 at the other axial end provides a support surface for the other layer of the two layers 10, 20. The aerosol entering the chamber via the aerosol inlet 210 passes along the passageway which in the first part is delimited by surface 241 of protrusion 240, the outer surface of the chamber and by the opposed layers 10 and 20.

Figure 3:
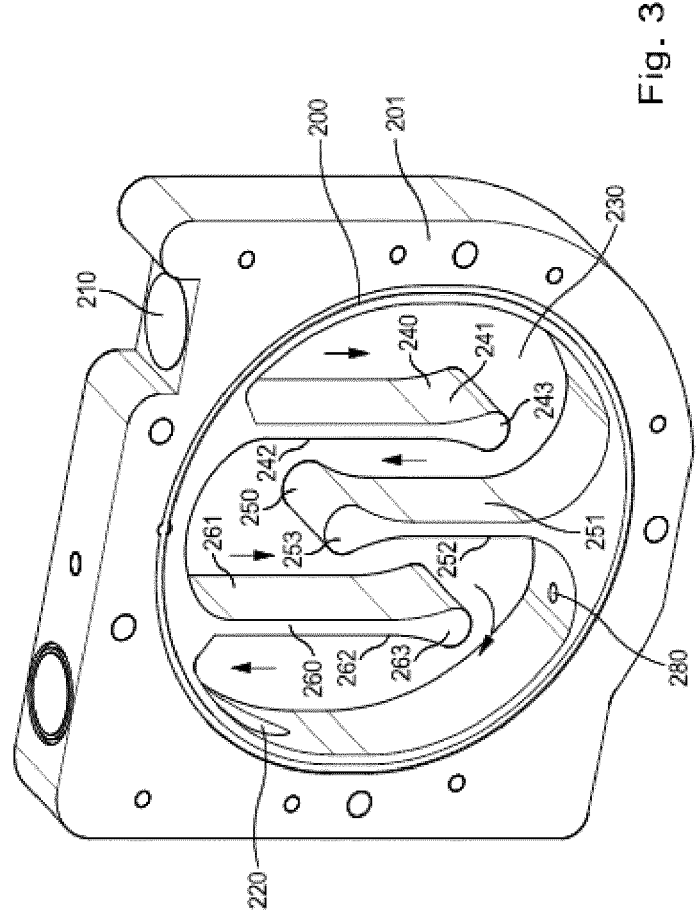
FIG. 3 shows a perspective view of an intermediate chamber of the humidifier through which the aerosol passes, the aerosol being humidified during the passage through the chamber.

As shown in FIG. 3, the neighbouring protrusion 250 protrudes from the opposite inner surface to the inside in such a way that a U-shaped passage is formed by protrusion 240 and 250. In the embodiment shown, a further protrusion 260 is shown which again extends from the upper lateral surface to the inside. As can be seen in FIG. 3, neighbouring protrusions extend from opposite sections of the lateral surface in such a way that the passageway follows a meandering pattern inside the chamber between the protrusions. Protrusion 250 comprises surfaces 251, 252 and protrusion 260 comprises surfaces 261, 262 which face the passageway. Accordingly, surfaces 241, 242, 251, 252, 261, and 262 are part of the first boundary surfaces of the passageway. A section of the first layer 10 which faces the passageway and delimits the passageway in the axial direction of the intermediate chamber builds a second boundary surface of the passageway. In the same way a section of the second layer 20 which delimits the passageway in the axial direction of the intermediate chamber builds a third boundary surface of the passageway. Furthermore, the inner surfaces of the cylindrically shaped intermediate chamber facing to the inside of the chamber and provided inter alia on the right side after the aerosol inlet 210 in the direction of flow and on the left side before the aerosol outlet 220 further delimit the passageway. Thus, inside the intermediate chamber the passageway is delimited by the first boundary surfaces, the second boundary surface, the third boundary surface, and the inner surfaces of the cylindrically shaped intermediate chamber. The end surfaces 253 and 263 again provide support surfaces for the first layer and for the second layer. As can be seen in FIG. 3, the passageway is mainly formed by the inner surface of the lateral wall and by walls of the protrusions 240, 250, 260, i.e. walls 241, 242, 251, 252 and walls 261, 262. Depending on the desired length of the passageway, which, among others, may be chosen in accordance with the intended flow of the aerosol, the intended temperature of the water in the water compartments, the intended degree of humidification of the aerosol, and other factors, the number of protrusions can be varied. While in the shown embodiment three protrusions have been selected, of course alternative embodiments with different numbers of protrusions are possible. For example, the number of protrusions could be 1, 2, 4, 5, 6, 7, 8, 9 or any other number. In cases where the aerosol flow into the humidifier (through aerosol inlet 210) is desired to be opposite (antiparallel) to the aerosol flow out of the humidifier (through aerosol outlet 220), the number of protrusions is preferably uneven (e.g., 1, 3 or 5). On the other hand, in cases where the aerosol flow into the humidifier is intended to have the same direction as the aerosol flow out of the humidifier, an even number of protrusions is preferred (e.g., 2 or 4).

In the embodiment shown, three protrusions are used so that inside the passageway the aerosol 310 changes the direction to the opposite flow direction. The number of protrusions may, however, depend on the length of the passageway needed to humidify the aerosol and to heat the aerosol.

As can be seen in FIG. 3, the aerosol is directly passed along the two layers 10, 20 which close the passageway in the axial direction of the chamber. The two layers 10, 20 seal the passageway in the axial direction and the two membranes are pressed against the support surfaces of the projecting surfaces by the hydrostatic pressure of the water in the water chambers. The aerosol is humidified by passing along the layers 10, 20.

The aerosol inlet 210 and the aerosol outlet 220 are both provided on the upper lateral surfaces. Opposite to the aerosol outlet 220, an opening 280 is provided at a lower part of the passageway where condensed liquid generated in the heated aerosol can be collected and can exit the passageway. The water outlet is provided on a lateral surface of the intermediate chamber, preferably on a lateral surface opposite to the inlet and outlet. With an orientation of the humidifier and the intermediate chamber as shown in FIG. 3, the aerosol inlet and the aerosol outlet are located on an upper part of the lateral surface, whereas the opening for removal of the condensed liquid is provided on the lower lateral surface.

In the embodiment shown in FIG. 3, the passage comprises two sections where the opening 280 could be provided. As shown in FIG. 3 it is provided at the lower section of the passage which is closer to the outlet 220.

As can be deduced from FIGS. 1 and 3, the water vapor entering into the passageway 230 enters the passageway in opposite direction. The water vapor from the first water compartment 100 will enter the passageway mainly in an axial direction of the cylindrically shaped intermediate chamber, whereas the water vapor from the second water compartment will also enter the passageway mainly in the axial direction perpendicular to the flow. However, the water vapor from the first water compartment 100 and the second water compartment 300 have a momentum directed in opposite directions so that the net momentum applied to the aerosol to be humidified in the passageway is zero. As a consequence, the deposit of aerosolizable material on a surface opposite to the first layer or opposite to a second layer is avoided.

Figure 4:
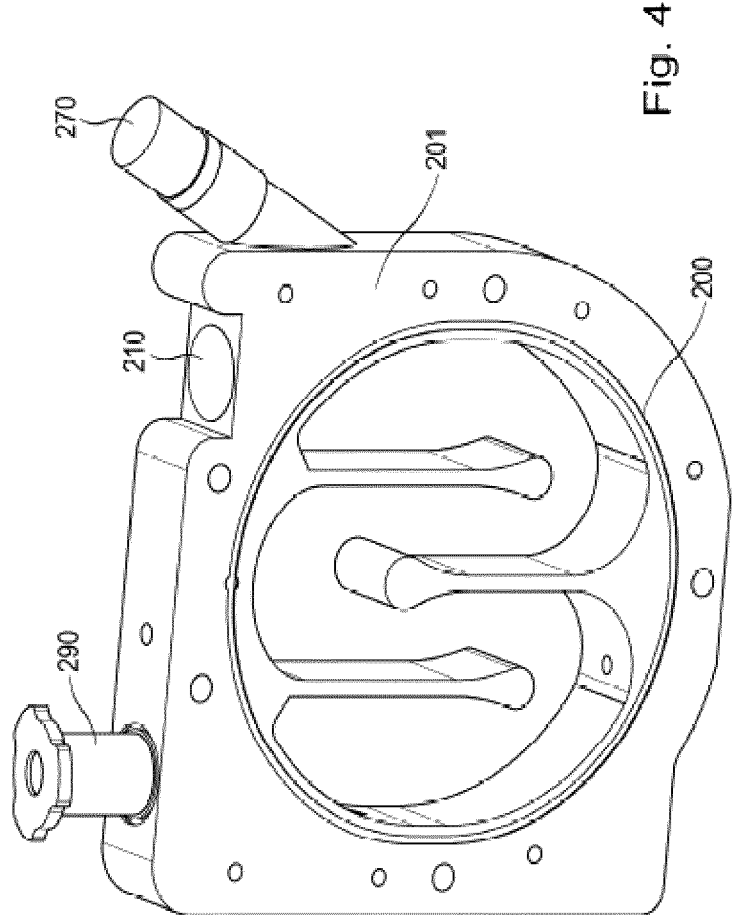
FIG. 4 shows the chamber of FIG. 3, additionally including an inlet for breathing air.

In FIG. 4 a further embodiment of the intermediate chamber 200 is shown. The embodiment shown in FIG. 4 differs from the embodiment of FIG. 3 in that a second inlet 270 is provided in the passageway configured for the inlet of breathing air into the passageway. As discussed in the introductory part of the description, the humidified aerosol may be administered to both spontaneously breathing patients and to mechanically ventilated patients and patients under ventilatory support. The embodiment shown in FIG. 4 is particularly suitable for aerosol administration to spontaneously breathing patients. When a humidified aerosol is provided to a patient for inhalation, it is preferred not only to humidify the aerosol but to also humidify the breathing air, because otherwise mixing humidified aerosol with non-humidified breathing air would inevitably lead to an undesirable drying of the humidified aerosol. The breathing air to be humidified enters the intermediate chamber through the second inlet 270 which is located below (or, when seen in the direction of the aerosol flow, after) the first inlet 210. The inlet for the breathing air is not located parallel to the inlet of the aerosol, but is angled relative to the inlet of the aerosol such that the breathing air will mix more efficiently with the aerosol entering through inlet 210. A tube is connected to the inlet 270 through which the breathing air can enter the chamber 200. Furthermore, a check valve may be provided in tube, the check valve making sure that, when the patient is exhaling, the aerosol does not leave the chamber 200 in the direction opposite to the flow direction of the aerosol. Upon the patient breathing in, the aerosol and the breathing air are mixed and they are both humidified, as explained above in connection with FIGS. 1-3, and are fed to the aerosol outlet. An exit connector 290 is provided at the aerosol outlet. This exit connector 290 can be used to connect cables or similar devices to the intermediate chamber 200 to further guide the humidified aerosol.

In another embodiment it is possible to provide a separate humidifier for the breathing air. In such an embodiment, a system as shown in FIG. 1 may be used separately for the breathing air such that not the aerosol enters the inlet 210, but only breathing air. In this embodiment the system shown in FIG. 1 may be provided twice, one for humidifying and heating the aerosol and the other for humidifying and heating the breathing air. This embodiment may be used when the breathing air is not compatible with the provided aerosol. The rest of the chamber shown in FIG. 4 corresponds to the chamber shown in FIG. 3 and is not explained in detail again.

As can be deduced from FIGS. 3 and 4, the intermediate chamber 200 with its substantially cylindrical shape has a larger radial extension than a longitudinal extension in a direction of a longitudinal axis of the cylindrical shape. In other words, the cylindrical shape of the intermediate chamber is such that the shape has a larger radial extension than a longitudinal extension.

The first and the second water compartment enclose the cylindrically shaped intermediate chamber in the axial direction, wherein the aerosol inlet and the aerosol outlet are located on a lateral surface of the cylindrically shaped intermediate chamber so that the aerosol passing through the passageway has substantially no components in the axial direction of the intermediate chamber, but only components perpendicular to the axial direction.

Figure 5:
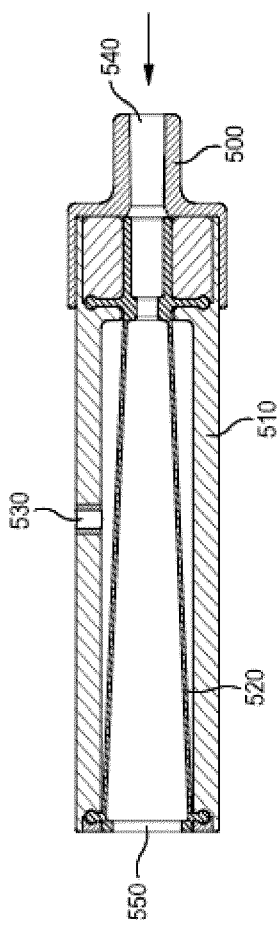
FIG. 5 is a schematic view of a nozzle which may be provided at an aerosol inlet of the chamber shown in FIG. 3.

In connection with FIG. 5, a nozzle 500 is explained in more detail which may be provided at the aerosol inlet 210 and through which then the aerosol to be humidified enters the passageway. The aerosol to be humidified enters the nozzle 500 as indicated by the arrow in FIG. 5 through opening 540 and leaves the aerosol by opening 550. The nozzle 500 comprises a housing 510 in which a passageway for the aerosol to be humidified is formed by an excitable membrane 520 which is designed in such a way that the passageway's cross section increases in flow direction. The membrane can be excited by pressure pulses which are used in the aerosolization device to generate the aerosol, and the membrane's excitation can help to prevent particles of the aerosol from adhering and agglomerating on the nozzle's inner walls. The term "membrane" refers to any sheet-like structure that is essentially impermeable to gas, liquid, and the aerosolizable material. The excitable membrane is designed such that it elastically deforms and oscillates in response to pressure pulses. These pressure pulses may come from the carrier gas supplied to the aerosolization device. However, the nozzle furthermore may comprise an opening 530 through which an external source for generating pressure pulses can be connected to the inside of the housing 510 to excite the membrane.

It has been found that the aerosol entering the humidifier tends to adhere at the inlet of the humidifier. If stiff walls are used at this part of the humidifier, the aerosol's particles can accumulate on the side walls. This would lead to a reduced opening of the aerosol inlet, which in turn would cause increased flow velocity and impede the proper functioning of the humidifier. However, modifying the inlet in the described way (i.e., providing a nozzle 500, the inner walls of which are formed by an excitable membrane 520) allows for (quasi-continuous) removal of unwantedly deposited particles by application of pressure pulses which, as explained above, may be applied to the system in order to generate the aerosol to be humidified. Preferably, the nozzle has a conical shape with a defined opening angle. The opening angle of the nozzle is between 5° and 15°, preferably between 7° and 11°, and more preferably 9°. The excitable membrane 520 may be a single membrane, but can also be formed by two separate membranes which connected together form the passageway for the aerosol passing through the nozzle.

Figure 6:
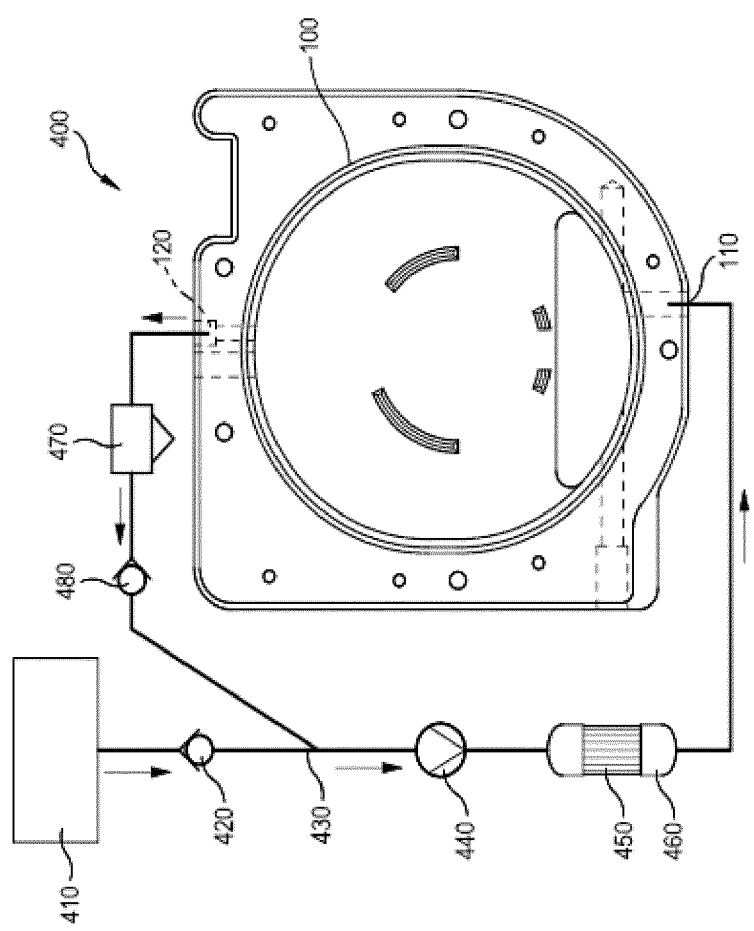
FIG. 6 is a schematic view of a water circuit used to heat the water passing through the water compartment of FIG. 2.

In connection with FIG. 6, an embodiment is disclosed in more detail where the water is not heated through the heating unit 130 shown in FIG. 1, but where the water is heated through a water circuit which circulates water through a water compartment such as water compartment 100. In the embodiment shown in FIG. 6, the water circuit 400 allows water to circulate through the first water compartment 100. However, it should be understood that the same circuit 400 may also circulate the water through the second water compartment 300. In another embodiment one water circuit is provided for each water compartment.

The water circuit 400 comprises a heat exchanger 450 and a heating element 460 which heats the water circulating in the water circuit. The water circuit comprises a water reservoir 410 and check valve 420, through which the water can be supplied to the water circuit. At junction 430 the water, after having passed the water compartment 100, is fed back to the circuit. A pump 440 for pumping the water through the water circuit transfers the water to the heating element 460 and the heat exchanger 450. The water is then passed through water inlet 110, the water exiting the water compartment at the water outlet 120. As the water compartment, for its other functional features, corresponds to the water compartment discussed above in more detail in connection with FIG. 2, a more detailed discussion of the water compartment is avoided. A ventilation 470 can be provided through which air contained in the water circuit can exit the water circuit, especially when the water circuit is filled for the first time. A second check valve 480 assures the directional flow of the water in the water circuit. The pump 440 is designed in such a way that the flow velocity of the water is such that a desired temperature of the water inside the chamber is obtained, e.g. the water temperature of 40° C.-50° C. inside the water chamber as discussed above. For controlling the temperature, a temperature sensor may be provided in the water compartment such as the temperature sensor 150.

The above-discussed humidifier provides an efficient heating and humidification of an aerosol as an intermediate chamber providing the passageway for the aerosol to be humidified is sandwiched between two water compartments. The first and the second layer provide a large surface along which the aerosol will pass on its way through the intermediate chamber.

The invention claimed is:

1. A humidifier configured to humidify an aerosol, comprising:

a first water compartment containing water used to humidify the aerosol;

a second water compartment containing water used to humidify the aerosol;

an intermediate chamber sandwiched between the first water compartment and the second water compartment, the intermediate chamber comprising an aerosol inlet, an aerosol outlet, and at least two protrusions, and providing first boundary surfaces of a passageway through which the aerosol to be humidified passes;

a first layer permeable to water vapour and impermeable to liquid water, which is located between the first water compartment and the intermediate chamber, a section of the first layer providing a second boundary surface of the passageway;

a second layer permeable to water vapour and impermeable to liquid water, which is located between the second water compartment and the intermediate chamber, a section of the second layer providing a third boundary surface of the passageway opposed to the second boundary surface, and wherein the at least two protrusions each protrude from a lateral surface of the intermediate chamber to an inside of the intermediate chamber, the at least two protrusions being part of the first boundary surfaces and protruding into the inside of the intermediate chamber such that the passageway follows a meandering pattern inside the intermediate chamber between the at least two protrusions, and the at least two protrusions provide a support surface for each of the first layer and the second layer, the intermediate chamber has a substantially cylindrical shape with the lateral surface, the aerosol inlet and the aerosol outlet located on the lateral surface of the intermediate chamber, and the first water compartment and the second water compartment enclose the intermediate chamber in an axial direction defined by the substantially cylindrical shape of the intermediate chamber, and the at least two protrusions include a first protrusion and a neighboring second protrusion that protrude from opposite parts of the lateral surface into the inside of the intermediate chamber such that a U-shaped passage is formed by the first protrusion and the neighboring second protrusion, the passageway including the U-shaped passage.

2. The humidifier according to claim 1, wherein the passageway is delimited by the first boundary surfaces, the second boundary surface, and the third boundary surface and located in the intermediate chamber such that the aerosol passing through the passageway is flowing substantially perpendicular to the axial direction of the intermediate chamber.

3. The humidifier according to claim 1, wherein the first layer is arranged substantially parallel to the second layer.

4. The humidifier according to claim 1, wherein the aerosol inlet, the passageway, and the aerosol outlet are arranged such that the aerosol exiting the aerosol outlet has a flow direction which is substantially opposite to the flow direction of the aerosol entering the aerosol inlet.

5. The humidifier according to claim 1, wherein the first layer rests on a first support surface of the at least two protrusions and the second layer rests on a second support surface of the at least two protrusions opposite to the first support surface, the first and the second layer sealing neighbouring sections of the passageway from each other in the axial direction of the intermediate chamber.

6. The humidifier according to claim 1, wherein the intermediate chamber comprises a second inlet in the passageway configured for an inlet of breathing air into the passageway.

7. The humidifier according to claim 6, wherein the second inlet is located after the aerosol inlet in a direction of the flow of the aerosol in the passageway.

8. The humidifier according to claim 1, wherein the first water compartment and the second water compartment each comprise a heating unit for heating the water in the corresponding compartment.

9. The humidifier according to claim 1, further comprising:

a water circuit which circulates water through the first and the second water compartments.

10. The humidifier according to claim 9, wherein the water circuit comprises a pump for pumping the water through the water circuit and a heat exchanger configured to heat the water.

11. The humidifier according to claim 1, wherein each of the first and second water compartments comprises projections which guide the water circulating in the corresponding water compartment and build a further support surface for the first and second layer respectively.

12. The humidifier according to claim 1, wherein the intermediate chamber comprises in the passageway an opening for removal of condensed liquid, which is located in the lateral surface of the intermediate chamber.

13. The humidifier according to claim 1, wherein a nozzle is provided at the aerosol inlet through which the aerosol to be humidified enters the passageway, the nozzle having a cross section which increases in the flow direction of the aerosol, the nozzle comprising inner walls which comprise at least one excitable membrane which is configured to be excited by pressure pulses.

14. The humidifier according to claim 13, wherein the nozzle has a conical shape.

15. The humidifier according to claim 14, wherein the opening angle of the nozzle is between 5 and 15 degrees.

16. The humidifier according to claim 1, wherein each of the first and second water compartments has a substantially cylindrical shape with a lateral surface, each of the first and second water compartments comprising a water inlet at one side of the lateral surface, and a water outlet at an opposite side of the lateral surface.

17. The humidifier according to claim 1, wherein the humidifier has mirror symmetry relative to a plane which is perpendicular to the axial direction of the intermediate chamber.

18. The humidifier according to claim 1, wherein
the passageway is delimited by the first boundary surfaces, the second boundary surface, and the third boundary surface and located in the intermediate chamber such that the aerosol passing through the passageway is flowing substantially perpendicular to the axial direction of the intermediate chamber, and
the first boundary surfaces are between the second boundary surface and the third boundary surface, and the second boundary surface and third boundary surface are outside of the intermediate chamber and are abutting the intermediate chamber thereby sealing neighbouring sections of the passageway from each other in the axial direction of the intermediate chamber.

* * * * *